(12) United States Patent
Phillips et al.

(10) Patent No.: US 9,176,025 B2
(45) Date of Patent: Nov. 3, 2015

(54) APPARATUS AND METHOD OF VIBRATION TESTING FOR MANUFACTURING DEFECT DETECTION IN COMPOSITE INSULATORS

(71) Applicant: Electric Power Research Institute, Inc., Charlotte, NC (US)

(72) Inventors: Andrew John Phillips, Harrisburg, NC (US); Kristopher C. Kozak, San Antonio, TX (US)

(73) Assignee: Electric Power Research Institute, Inc., Charlotte, NC (US)

( * ) Notice: Subject to any disclaimer, the term of this patent is extended or adjusted under 35 U.S.C. 154(b) by 243 days.

(21) Appl. No.: 13/728,412

(22) Filed: Dec. 27, 2012

(65) Prior Publication Data

US 2013/0167615 A1    Jul. 4, 2013

Related U.S. Application Data

(60) Provisional application No. 61/580,803, filed on Dec. 28, 2011.

(51) Int. Cl.
| | |
|---|---|
| *G01M 99/00* | (2011.01) |
| *G01N 3/30* | (2006.01) |
| *G01N 3/40* | (2006.01) |

(52) U.S. Cl.
CPC .............. *G01M 99/007* (2013.01); *G01N 3/30* (2013.01); *G01N 3/40* (2013.01); *G01N 3/405* (2013.01)

(58) Field of Classification Search
CPC ....... G01M 99/007; G01N 3/405; G01N 3/40; G01N 3/30; G01N 3/303; G01N 3/307; G01N 3/34; G01N 3/00; G01N 3/02

USPC .................................. 73/12.01, 12.07, 12.09
See application file for complete search history.

(56) References Cited

U.S. PATENT DOCUMENTS

| | | | | |
|---|---|---|---|---|
| 4,442,697 | A | * | 4/1984 | Jones et al. .................. 73/12.14 |
| 5,229,952 | A | | 7/1993 | Galloway et al. |
| 5,770,791 | A | * | 6/1998 | Manahan, Sr. ............... 73/12.01 |
| 6,799,126 | B1 | * | 9/2004 | Ratcliffe et al. ................. 702/56 |

(Continued)

FOREIGN PATENT DOCUMENTS

| | | |
|---|---|---|
| RU | 1817838 | 5/1993 |
| RU | 2298777 | 5/2007 |

(Continued)

OTHER PUBLICATIONS

O. Schedrina, International Search Report for PCT/US2012/071974, Mar. 12, 2013, Russia.

*Primary Examiner* — Lisa Caputo
*Assistant Examiner* — Philip Cotey
(74) *Attorney, Agent, or Firm* — Trego, Hines & Ladenheim, PLLC

(57) ABSTRACT

The present application relates to an apparatus and method for detecting defects in composite insulators used in power systems. The apparatus includes a test frame, a hydraulic cylinder connected to a first end of the test frame for imparting a load on a composite insulator, a hammer for imparting excitations into the composite insulator, and a data collection device for collecting frequency responses traveling in the composite insulator as a result of the hammer striking the insulator. The composite insulator is secured between the hydraulic cylinder and a second end of the test frame.

4 Claims, 7 Drawing Sheets

(56) References Cited

U.S. PATENT DOCUMENTS

| | | | |
|---|---|---|---|
| 6,813,927 B1 * | 11/2004 | Harris et al. | 73/12.12 |
| 2004/0144158 A1 * | 7/2004 | Huang et al. | 73/12.01 |
| 2006/0005606 A1 * | 1/2006 | Hatanaka et al. | 73/12.14 |
| 2008/0060412 A1 * | 3/2008 | Palmer | 73/12.09 |
| 2009/0266141 A1 * | 10/2009 | Pratt | 73/12.12 |
| 2012/0151989 A1 * | 6/2012 | Knox et al. | 73/12.04 |

FOREIGN PATENT DOCUMENTS

| | | |
|---|---|---|
| SU | 1462361 | 2/1989 |
| SU | 1679357 | 9/1991 |

* cited by examiner under US 9,176,025 B2 — page 1/2

APPARATUS AND METHOD OF VIBRATION TESTING FOR MANUFACTURING DEFECT DETECTION IN COMPOSITE INSULATORS

BACKGROUND OF THE INVENTION

The present invention relates generally to the detection of manufacturing defects in composite insulators and, more particularly, to an apparatus and method for detecting defects in composite insulators used in power systems.

Composite insulators consist of a fiberglass rod with two metal end fittings attached. The rod is then coated with rubber material protecting the rod from the environment. It is possible that during the manufacturing process the rod is partially damaged and may result in a failure in the field (may happen many years after installation). The damage may occur while either the end fittings are being attached to the rod (usually by crimping), while the rubber material is being molded on, or during handling (especially when the rod is hot after molding).

For a number of years, investigations of vibration-based field inspection methods have been conducted to identify damaged insulators (both NCI and porcelain–note NCI=non-ceramic insulator=composite insulator=polymer insulator). After several investigations were performed on composite insulators, it was determined that while insulator damage could be detected in a vibration response, a number of variables, such as tension load and attachments, could affect the vibration response more strongly than the damage. This has made the technique challenging, almost impossible, to apply in field situations. For this reason, vibration-based inspection is best suited for a laboratory-type environment rather than a field installation.

Currently, two types of tests are used in the manufacturing process to identify potential rod defects: (1) To listen to acoustic signals while crimping the end fitting on to the rod—if the rod cracks or is over crimped a specific signal is identified, and (2) perform a Routine Test Load (RTL) test.

The RTL is performed at the end of the manufacturing process. All units are required to be subjected to an RTL which is 50% of their specified mechanical Load. This is a proper time to conduct the RTL since the geometry is well defined as is the mechanical load. However, while the RTL test provides a basis for mechanical strength, it has deficiencies in detecting defects in composite insulators.

BRIEF SUMMARY OF THE INVENTION

These and other shortcomings of the prior art are addressed by the present invention, which provides an apparatus and method for testing insulators for manufacturing defects.

According to one aspect of the invention, an apparatus for testing composite insulators includes a test frame, a hydraulic cylinder connected to a first end of the test frame for imparting a load on a composite insulator, a hammer for imparting excitations into the composite insulator; and a data collection device for collecting frequency responses traveling in the composite insulator as a result of the hammer striking the insulator. The composite insulator is secured between the hydraulic cylinder and a second end of the test frame.

According to another aspect of the invention, a method of testing composite insulators for manufacturing defects includes the steps of subjecting a composite insulator to a predefined load, using a hammer to impart excitations in the composite insulator, measuring the excitations, and analyzing the excitations and comparing the excitations to known good or bad composite insulator excitations.

A method of testing composite insulators for manufacturing defects includes the steps of providing a testing apparatus having a test frame having first and second ends, a hydraulic cylinder connected to a first end of a test frame, and a mass connected to a second end of the test frame. The method further includes the steps of connecting a first end of a composite insulator to the hydraulic cylinder and a second end of the composite insulator to the mass, attaching accelerometers to an end fitting of the composite insulator, using the hydraulic cylinder and mass to subject the composite insulator to a predefined test load, using a hammer to impart excitations into the composite insulator, measuring the excitations using the accelerometers, using a data collection device to receive signals from the accelerometers representative of the measured excitations, and analyzing the signals to determine the condition of the composite insulator.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
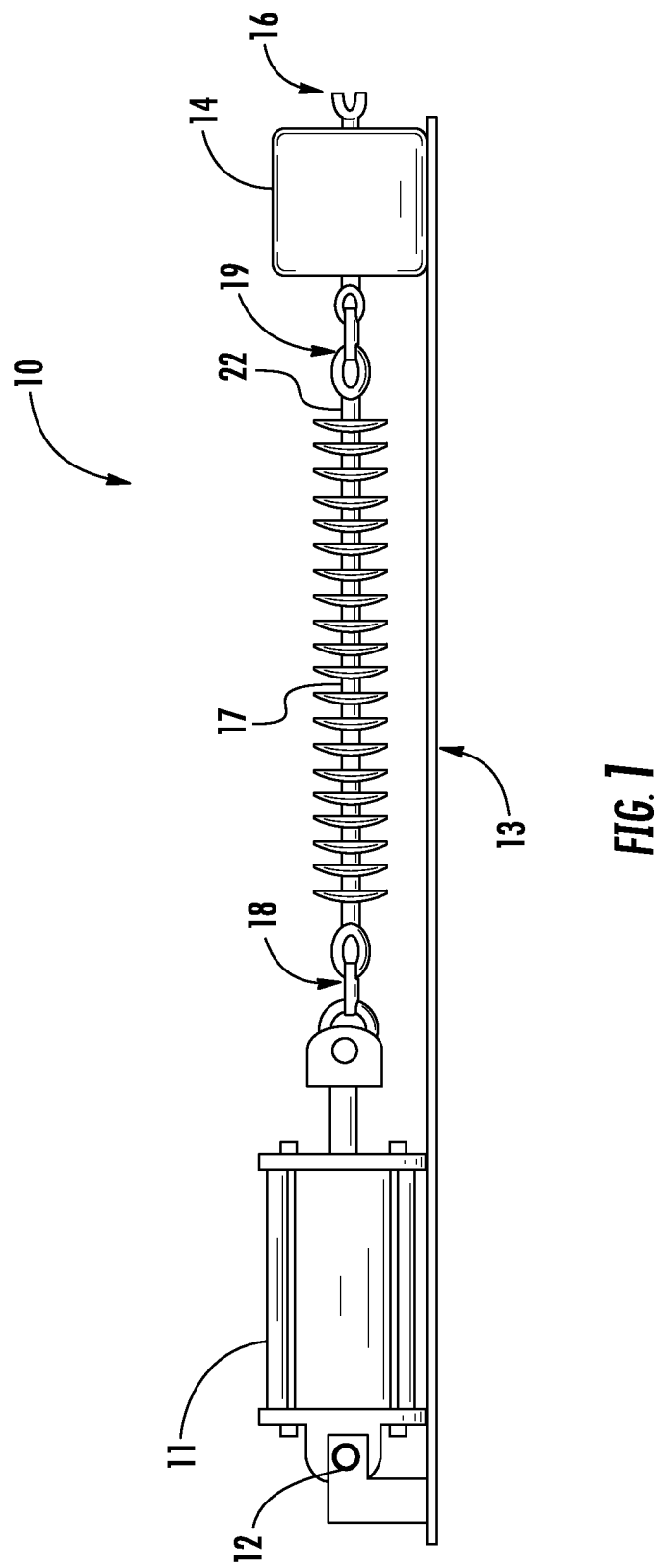
FIG. 1 shows an insulator in an RTL test rig.
Figure 2:
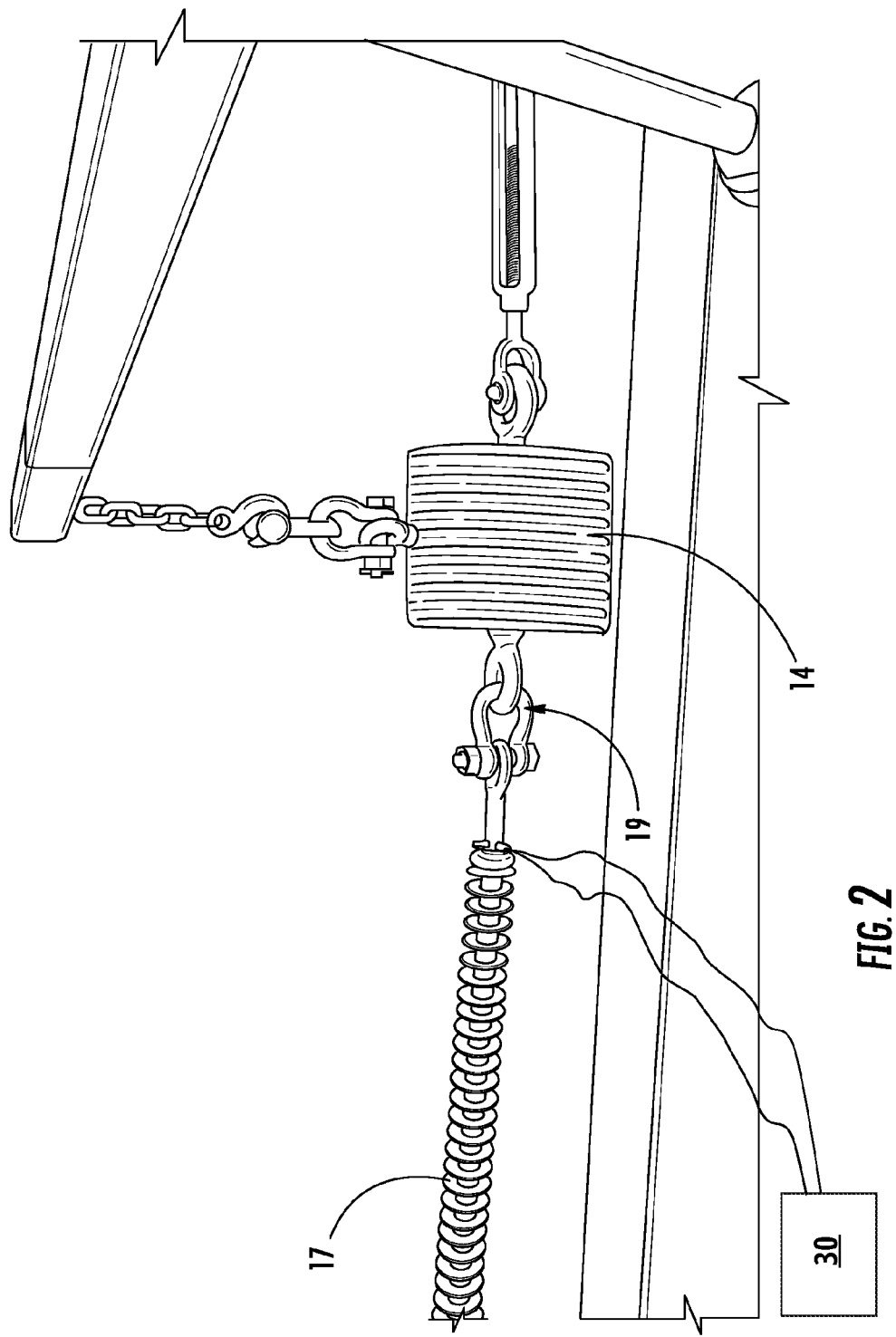
FIG. 2 shows a mass insulating insulator of the test rig of FIG. 1.
Figure 3:
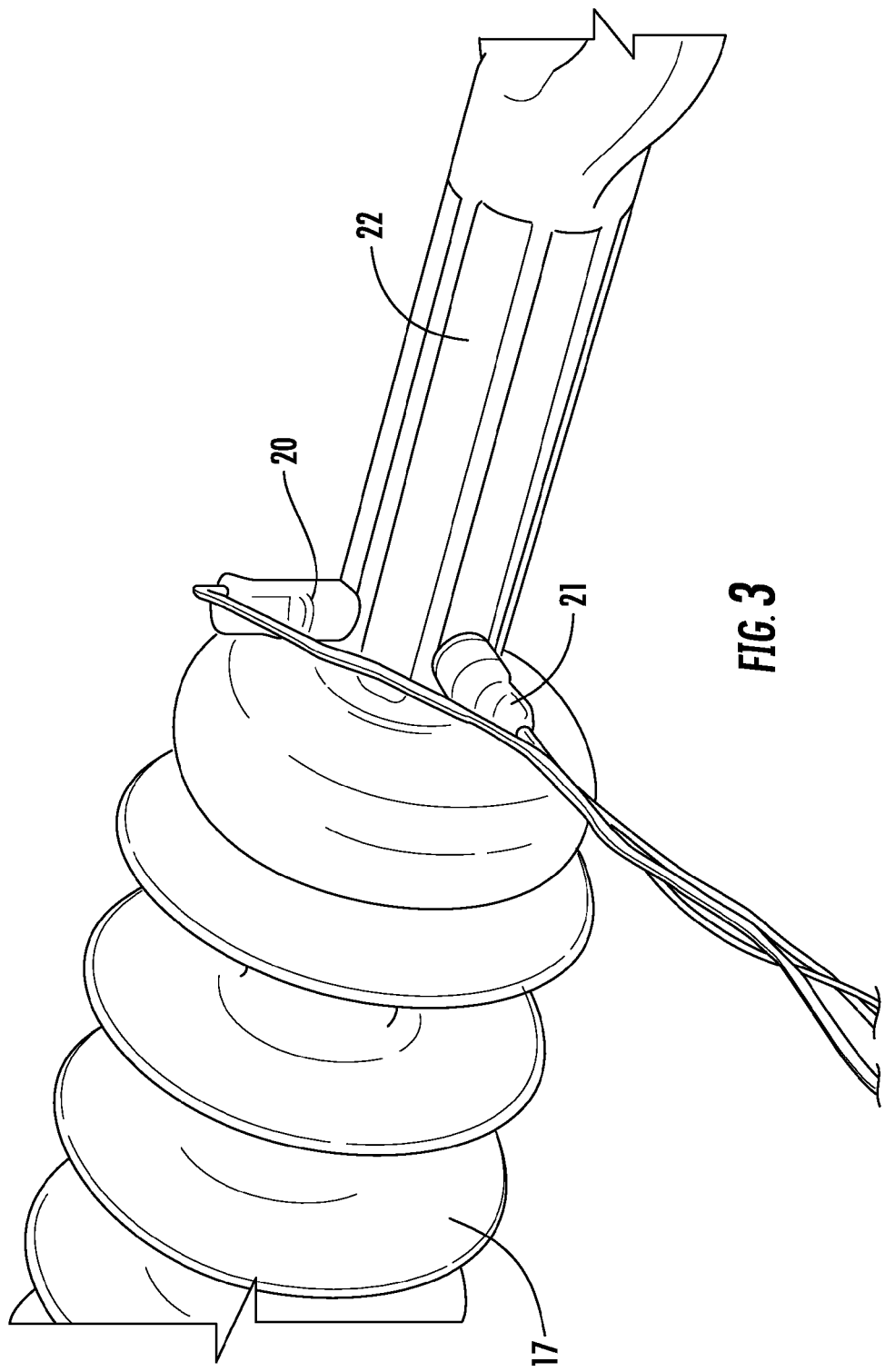
FIG. 3 shows accelerometers attached to an end fitting of the insulator of FIG. 1.

Referring now to the drawings, an exemplary apparatus for performing an RTL test and for detecting defects in composite insulators according to an embodiment of the invention is illustrated in FIGS. 1 and 2 and shown at reference numeral 10. The apparatus 10 includes a hydraulic cylinder 11 connected to a first end 12 of a test frame 13 and an impedance mass 14 connected to a second end 16 of the test frame 13. As shown, a composite insulator 17 is positioned between the cylinder 11 and the mass 14, thereby interconnecting the cylinder 11 and mass 14 such that a load can be imparted upon the insulator 17.

Once the insulator 17 is connected at a first end 18 to the hydraulic cylinder 11 and at a second end 19 to the mass 14, a predefined load is applied to the insulator 17. The mass 14 isolates the insulator 17 from the frame 13 and cylinder 11 to prevent responses from the frame 13 and cylinder 11 being mixed with the insulator 17 response. It should be appreciated that the mass 14 may be removed from the apparatus to allow the second end 19 to be connected directly to the second end 16 of the test frame. It should also be appreciated that the mass 14 may be varied in weight/mass depending on the testing being conducted.

Referring to FIGS. 3-8, once the insulator 17 is connected between the cylinder 11 and mass 14, accelerometers 20 and 21 are attached to end fitting 22 of the insulator 17 and connected to a data collection device, such as processor 30, to measure responses/excitations/pulses from the insulator during the test. Also, microphones may also be positioned near the fitting 22 to measure sound levels of the responses.

Figure 4:
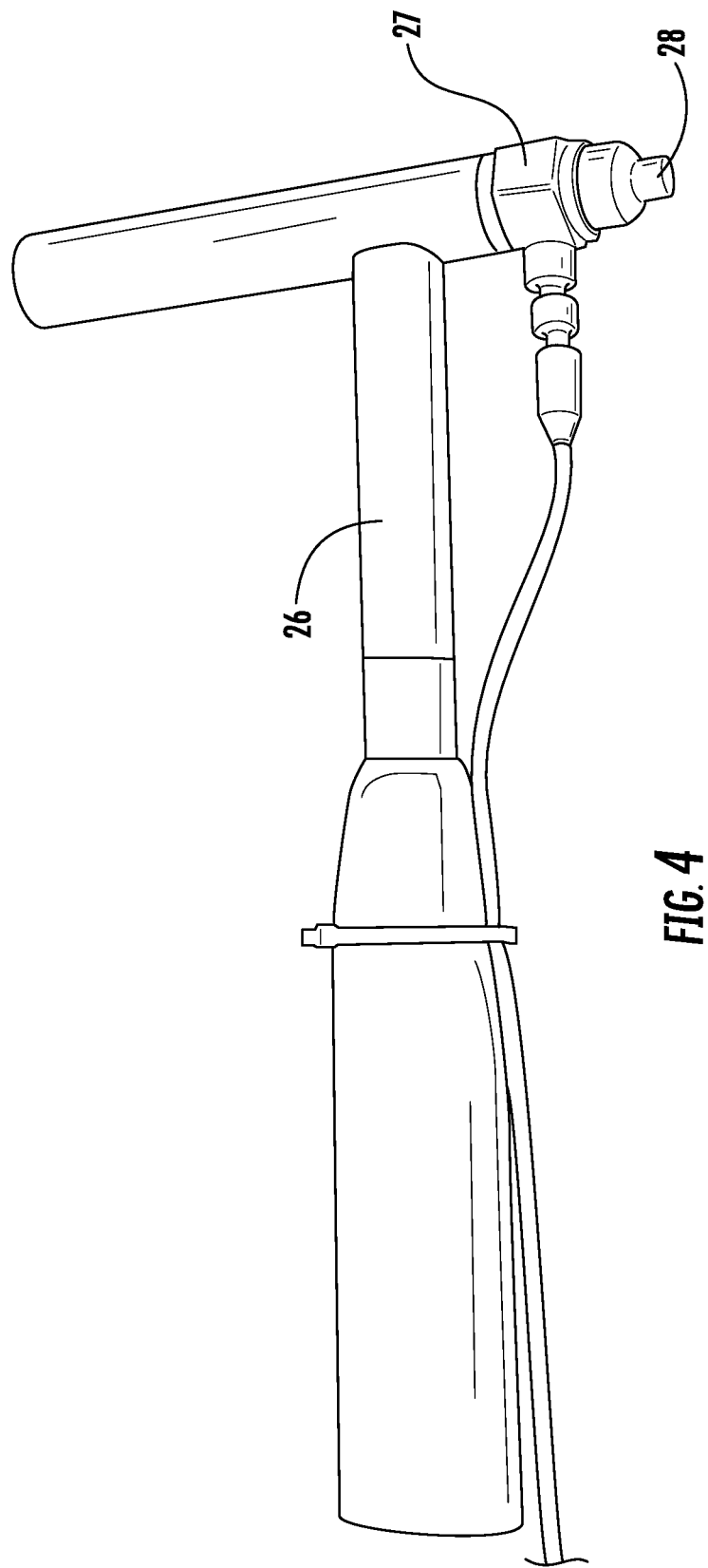
FIG. 4 shows a hammer used to excite the insulator of FIG. 1.
Figure 5:
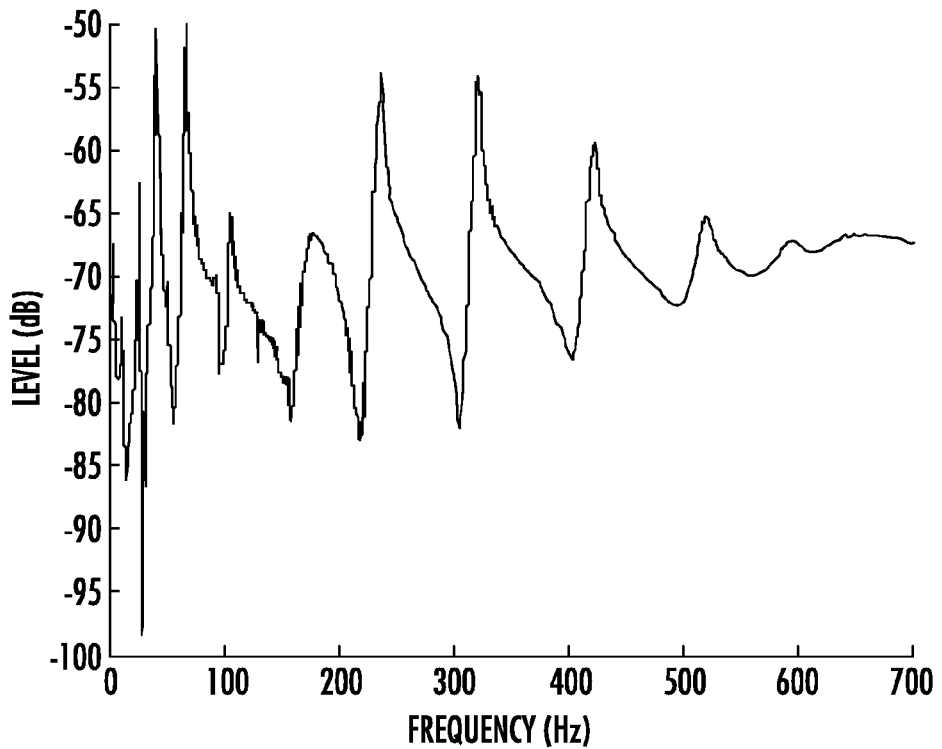
FIG. 5 illustrates an example frequency response.

While the RTL test is being performed, a hammer 26, FIG. 4, is used to excite the insulator 17 by striking the end fitting 22. The hammer 26 includes a force transducer 27, connected to processor 30, for determining the amount of force applied by the hammer 26 and an interchangeable tip 28. Once the insulator is struck with the hammer 26, a response of the insulator 17 may be measured using the accelerometers 20 and 21 (microphones may also be incorporated) and then converted to a frequency domain using a transform—Fourier, FIG. 5. The excitation from the hammer 26 may be measured by force transducer 27 attached to the hammer. It should be appreciated that the frequency response may be calculated based on accelerometer output or a combination of accelerometer output and input from the transducer to provide better signals and data. It should also be appreciated that one or more accelerometers may be used in different locations and planes. Further, it should be appreciated that signals transmitted by the accelerometers and force transducer, including frequency response, are transmitted to the processor 30 for data collection and analysis.

Figure 6:
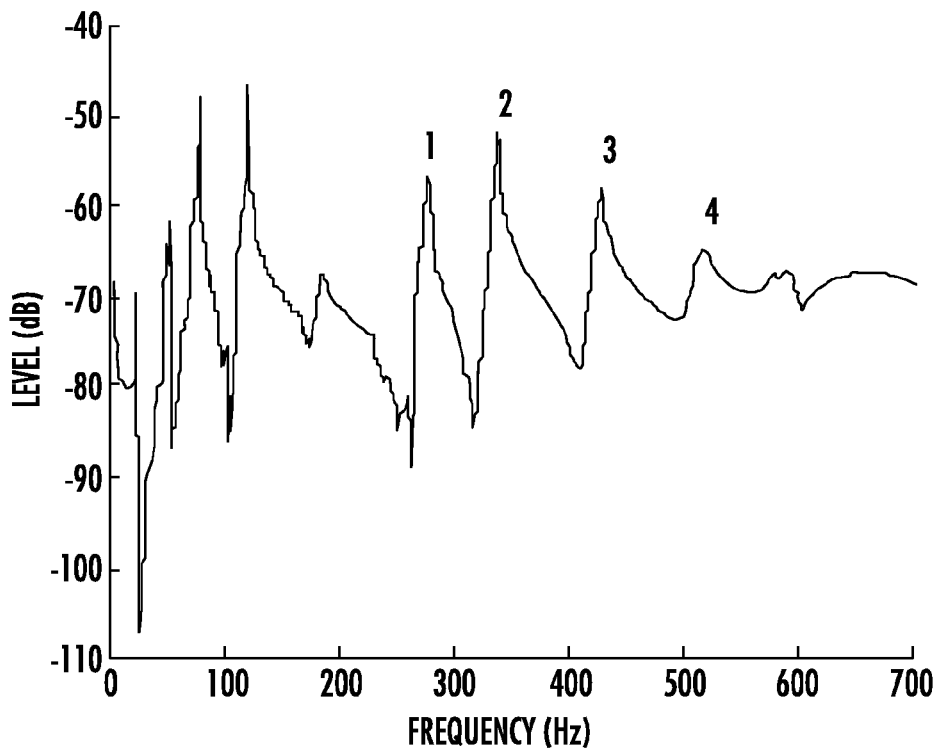
FIG. 6 illustrates how resonant frequencies are identified.
Figure 7:
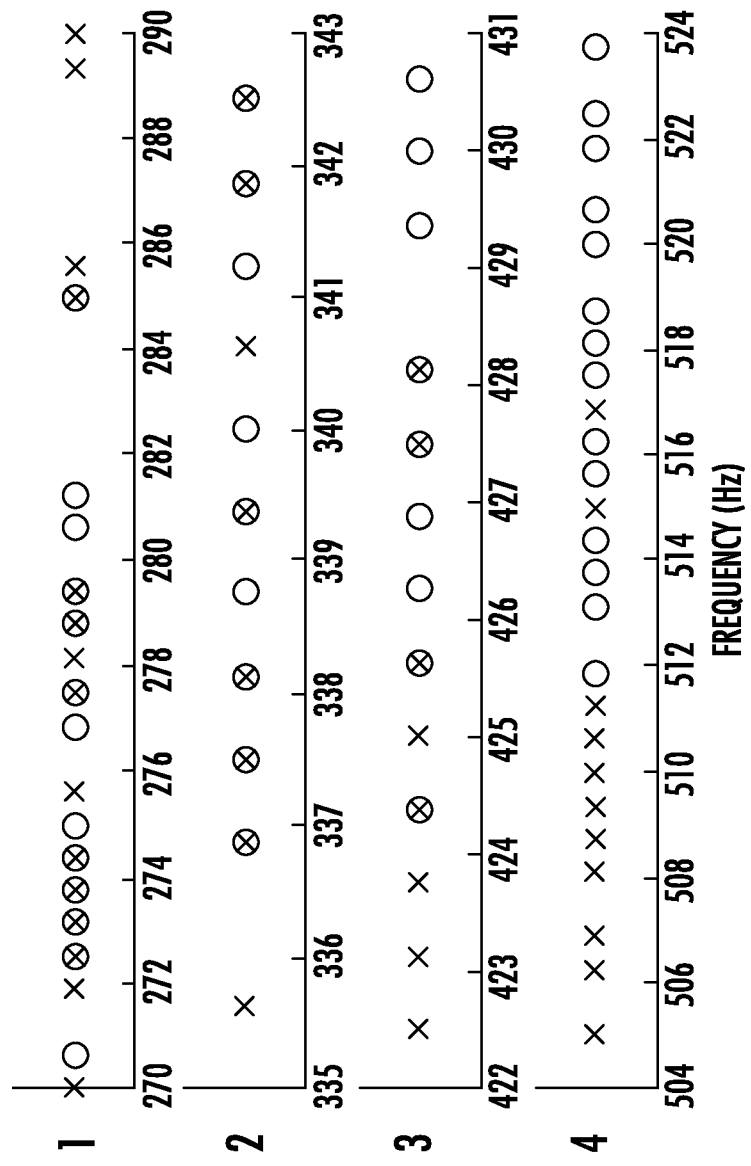
FIG. 7 shows $1^{st}$ four resonant frequencies for good and bad units.

The resonant frequencies are then identified, FIG. 6, and the frequencies of interest measured, FIG. 7. The frequencies of interest are determined by insulator dimensions and applied load on the insulator.

Figure 8:
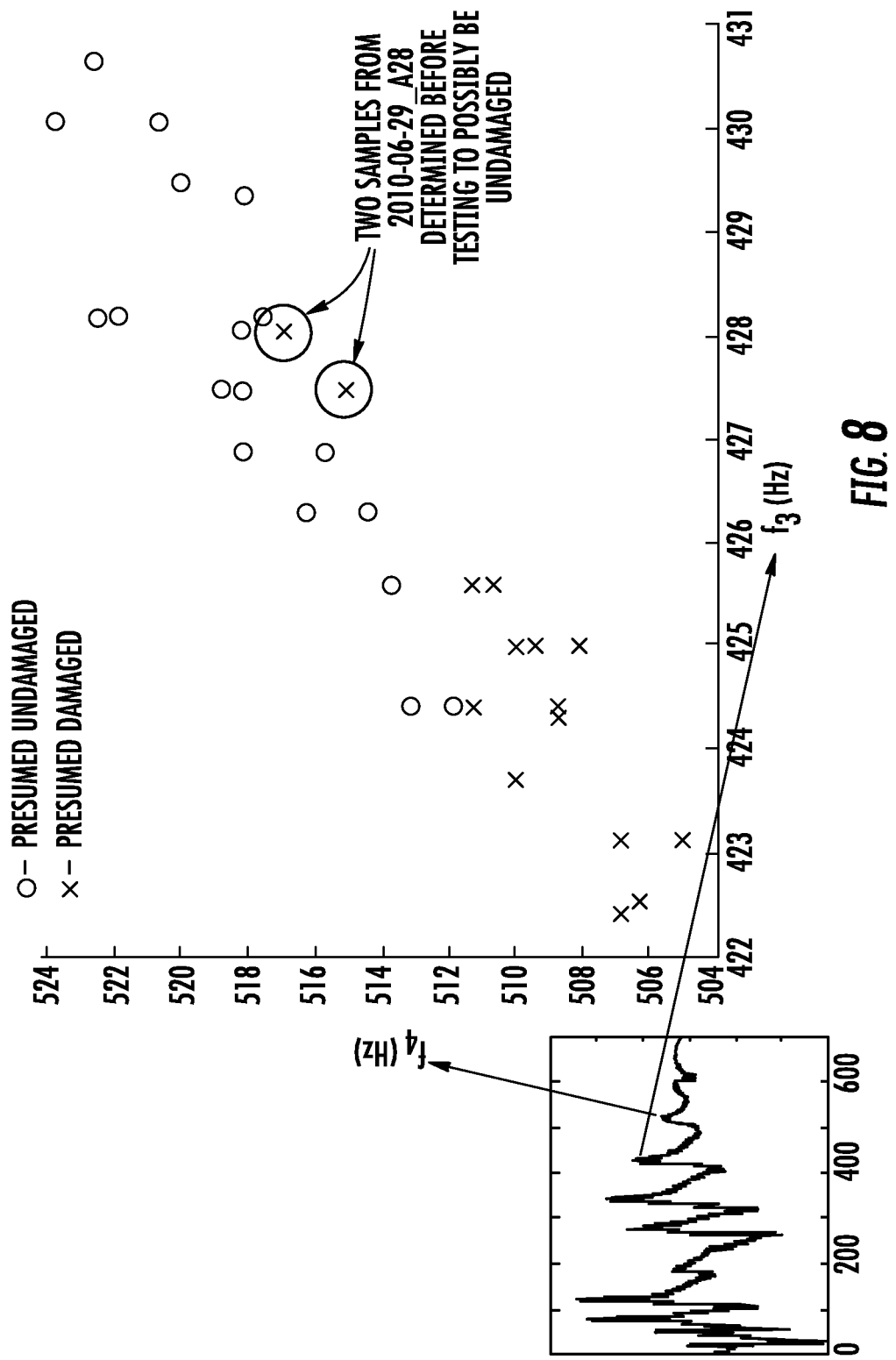
FIG. 8 shows two resonant frequencies plotted against each other to indentify a defective insulator.

An algorithm performed by the processor 30 is then used to determine whether the insulator 17 is good or bad. It may involve multiple resonant frequencies utilized in AND/OR statements. For example, FIG. 8 shows how the use of $3^{rd}$ and $4^{th}$ modes from FIG. 7 are used together. The threshold limits for the resonant frequencies are then determined by (1) determining a frequency response of a population of known good units of one design, (2) determining a frequency response of a population of known bad units of the same design, (3) developing a chart for specific designs that would list the acceptable range of each resonant response as well as the AND/OR algorithms, and (4) comparing the test results of insulators of the same deign against the chart and determining if the unit is good or bad (i.e., a defective rod or rod/end fitting interface). Additionally, testing of a large population of a specific insulator design to obtain an average and then identifying an insulator that significantly deviates from the average as a bad insulator may be performed.

The foregoing has described an apparatus and method of vibration testing for manufacturing defect detection of composite insulators. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

We claim:

1. An apparatus for testing composite insulators, comprising:
    (a) a test frame having spaced-apart first and second ends;
    (b) a hydraulic cylinder connected to the first end of the test frame;
    (c) a composite insulator connected to the hydraulic cylinder and the second end of the test frame, with the hydraulic cylinder and composite insulator are disposed in a parallel, in-line configuration to each other;
    (d) a hammer for imparting non-destructive excitations into the composite insulator; and
    (e) one or more accelerometers attached to the composite insulator for collecting frequency responses traveling in the composite insulator as a result of the hammer striking the insulator.

2. The apparatus according to claim 1, further including a mass positioned between and connected to the composite insulator and the second end of the test frame, the mass sufficient to isolate a vibration response of the test frame from a vibration response of the composite insulator.

3. The apparatus according to claim 1, wherein multiple accelerometers are positioned on an end fitting of the composite insulator to measure the excitations imparted by the hammer.

4. The apparatus according to claim 1, further including a force transducer positioned at a tip of the hammer for determining the amount of force applied by the hammer to the insulator.

* * * * *